(12) United States Patent
Shibanuma et al.

(10) Patent No.: US 6,300,531 B1
(45) Date of Patent: *Oct. 9, 2001

(54) FLUORINATION CATALYST AND PROCESS FOR FLUORINATING HALOGENATED HYDROCARBON

(75) Inventors: Takashi Shibanuma; Yoshio Iwai; Satoshi Koyama, all of Osaka (JP)

(73) Assignee: Daikin Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/435,178

(22) Filed: May 5, 1995

Related U.S. Application Data

(60) Division of application No. 08/052,684, filed on Apr. 27, 1993, which is a continuation-in-part of application No. 07/886,822, filed on May 22, 1992, now abandoned.

(30) Foreign Application Priority Data

May 24, 1991 (JP) .................................... 9-120132

(51) Int. Cl.$^7$ .................................................. C07C 17/08
(52) U.S. Cl. ............................................. 570/169
(58) Field of Search ............................................. 570/169

(56) References Cited

U.S. PATENT DOCUMENTS

| | | |
|---|---|---|
| 2,745,886 | 5/1956 | Ruh et al. . |
| 2,885,427 | 5/1959 | Ruh et al. . |
| 3,426,009 | 2/1969 | Chapman et al. . |
| 3,644,545 | 2/1972 | Buckman . |
| 3,755,477 | 8/1973 | Firth et al. . |
| 4,158,675 | 6/1979 | Potter . |
| 4,311,863 | 1/1982 | Gumprecht . |
| 4,439,534 | 3/1984 | Foulletier . |
| 4,748,285 | 5/1988 | Foulletier . |
| 4,766,259 | 8/1988 | Manzer et al. . |
| 4,792,643 | 12/1988 | Sobolev . |
| 4,828,818 | 5/1989 | Carlson et al. . |
| 4,876,406 | 10/1989 | Foulletier . |
| 4,912,270 | * 3/1990 | Carlson et al. ................. 570/169 |
| 5,281,568 | * 1/1994 | Scott et al. ..................... 570/169 |
| 5,849,658 | 12/1998 | Shibanuma et al. . |

FOREIGN PATENT DOCUMENTS

| | | |
|---|---|---|
| 0055652 | 7/1982 | (EP) . |
| 0055958 | 7/1982 | (EP) . |
| 0516000A1 | 12/1992 | (EP) . |
| 901297 | 7/1962 | (GB) . |
| 976883 | 12/1964 | (GB) . |
| 1091103 | 11/1967 | (GB) . |
| 1307224 | 2/1973 | (GB) . |
| 1589924 | 5/1981 | (GB) . |

OTHER PUBLICATIONS

Can. J. Chem., vol. 61, pp. 457 to 460 (1983).
Journal of Physical Chemistry, vol. 71, No. 13, pp. 4580–4581 (Dec. 1967).
Adsorption: Science and Technology; editors: A. E. Rodrigues et al., (1989) Proceedings of the NATO Advanced Study Institute on Adsorption: Science and Technology, pp. 3–14.
Powder Surface Area and Porosity; S. Lowell et al., 3$^{rd}$ Edition (1984) pp. 227–234.
Analytical Chemistry – The Working Tools; Strouts et al. vol. 1, pp. 118–122 (1955).
Ullmann's Encyclopedia of Industrial Chemistry, 5$^{th}$ Edition, vol. A7, pp. 76–77 (1986).
Journal of Colloid and Interface Science, vol. 51, No. 2, pp. 335–337 (May 1975).
Journal of Colloid and Interface Science, vol. 64, No. 1, pp. 192–193 (Mar. 15, 1975).
Bulletin de la Societe chimique de France (1984), No. 3–4, pp. I–91 to I–96.

* cited by examiner

Primary Examiner—Alan Siegel
(74) Attorney, Agent, or Firm—Birch, Stewart, Kolasch & Birch, LLP

(57) ABSTRACT

A fluorination catalyst comprising chromium oxide having a specific surface area of from 170 m$^2$/g to 300 m$^2$/g, which can catalyze the fluorination of a halogenated hydrocarbon with hydrogen fluoride and has a high activity and a long catalyst life.

20 Claims, 3 Drawing Sheets

FLUORINATION CATALYST AND PROCESS FOR FLUORINATING HALOGENATED HYDROCARBON

This application is a divisional of application Ser. No. 08/052,684 filed on Apr. 27, 1993, which is a Continuation-in-Part of Ser. No. 07/886,822 filed May 22, 1992, which is now abandoned, the entire contents of which are hereby incorporated by reference.

BACKGROUND OF THE INVENTION

1. Field of the Invention

The present invention relates to a fluorination catalyst and a process for fluorinating a halogenated hydrocarbon in a gas phase in the presence of the fluorination catalyst.

2. Description of the Related Art

Fluorinated halohydrocarbons such as 1,1,1,2-tetrafluoroethane are useful as substitutes for fluorocarbons and used as a refrigerant, a blowing agent, a propellant, a cleaning agent, and the like.

As a fluorination catalyst, chromium oxide which may be supported on alumina is known (see Japanese Patent Publication Nos. 10310/1964, 3004/1967 and 44973/1987, U.S. Pat. Nos. 3,426,009, 3,755,477 and 4,158,675 and GB 1 589 924). Also, fluorination in the presence of a chromium salt or partially fluorinated chromium oxide which may be supported on a carrier is known (see U.S. Pat. Nos. 2,745,886 and 2,885,427, DE Patent No. 1 252 182, Japanese Patent Publication No. 54503/1976, Japanese Patent Kokai Publication No. 132549/1978 and WO89/10341).

There are also known a catalyst comprising chromium oxide and an additive such as NaF (U.S. Pat. No. 3,644,545), Mg or Ba (Japanese Patent Publication No. 43922/1974), a transition metal (U.S. Pat. No. 4,792,643) or $AlPO_4$ (Japanese Patent Publication No. 17413/1989). Further, there are known processes using a catalyst comprising metal chromium (Japanese Patent Kokai Publication Nos. 19038/1985 and 221338/1989) or a metal other than chromium (Japanese Patent Kokai Publication Nos. 186945/1987, 268651/1989, 172933/1990 and 95438/1990).

U.S. Pat. No. 4,766,259 discloses a fluorination reaction using partially fluorinated aluminum oxide.

A liquid phase fluorination reaction using a Sb catalyst is known. In addition, a liquid phase fluorination reaction using an alkali metal fluoride as a catalyst is known (see U.S. Pat. No. 4,311,863 and Japanese Patent Kokai Publication No. 228925/1989).

As the halogenated hydrocarbons, various compounds are used. The fluorination is explained by making reference to preparation of 1,1,1,2-tetrafluoroethane (hereinafter referred to as "134a") by the fluorination of trichloroethylene or 1,1,1-tetrafluorochloroethane (hereinafter referred to as "133a").

It is not advantageous to synthesize 134a from 133a by a liquid phase reaction in view of a low conversion and a material of a reactor. When this fluorination reaction is carried out in a gas phase, conversion of 133a to 134a is low due to equilibrium. Therefore, a catalyst to be used should catalyze this reaction at a relatively low conversion and have a sufficiently long life and a good selectivity in an industrial use. Prolongation of the catalyst life avoids frequent change of the catalyst and lowers the catalyst cost.

The catalyst life can be prolonged by the addition of chlorine gas (Japanese Patent Publication No. 33604/1977) or oxygen gas (GB Patent No. 2 030 981 and Japanese Patent Kokai Publication Nos. 82206/1976 and 272535/1989) to a reaction gas mixture. When the chlorine gas is added, selection of a material of a reactor may be limited and also increase in by-products will be considered. When the oxygen gas is added, a conversion may be decreased.

In view of the above, it is advantageous to provide a catalyst which has a long life as such. When such catalyst is excellent in catalytic activity, not only the catalyst cost but also a size of a reactor which is made of an high quality expensive material can be reduced advantageously.

SUMMARY OF THE PRESENT INVENTION

One object of the present invention is to provide a novel fluorination catalyst which can effectively catalyze the fluorination of a halogenated hydrocarbon.

Another object of the present invention is to provide a process for fluorinating a halogenated hydrocarbon in a gas phase.

According to a first aspect of the present invention, there is provided a fluorination catalyst comprising chromium oxide having a specific surface area of from 170 $m^2/g$ to 300 $m^2/g$.

According to a second aspect of the present invention, there is provided a process for fluorinating a halogenated hydrocarbon in the presence of the above fluorination catalyst of the present invention.

DETAILED DESCRIPTION OF THE INVENTION

Figure 1A:
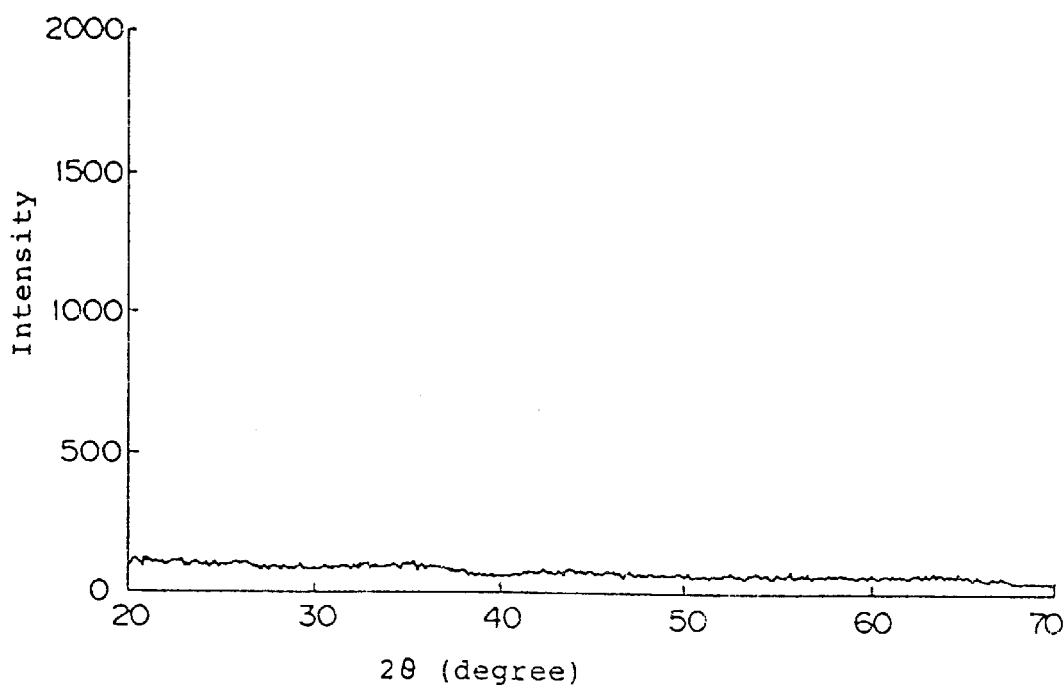
FIGS. 1A and 1B are x-ray diffraction patterns of amorphous chromium oxide and crystalline chromium oxide respectively.

Chromium oxide which is used as the catalyst according to the present invention is preferably amorphous. Herein, "amorphous" intends to mean that there is no substantial peak in an x-ray diffraction pattern of chromium oxide.

Preferably chromium oxide is partially fluorinated.

In the present invention, with control of properties of the catalyst in the preparation steps, a fluorination catalyst having a high activity and a long life, namely high productivity in comparison to the conventional catalysts can be produced. The catalyst may be activated with an oxygen-containing gas such as air.

In a preferred embodiment, a composition of chromium oxide is as follow:

When chromium oxide is expressed by the formula: $Cr_2O_3 \cdot nH_2O$, n is not larger than 3, preferably from 1 to 1.5. In chromium oxide, an atomic ratio of oxygen to chromium is not larger than 3:1, preferably from 2:1 to 2.75:1, more preferably from 2:1 to 2.3:1.

The chromium oxide catalyst of the present invention may be prepared as follows:

First, an aqueous solution of a chromium salt (e.g. chromium nitrate, chromium chloride, chrome alum, chromium sulfate, etc.) and aqueous ammonia are mixed to precipitate chromium hydroxide. For example, to a 5.7% aqueous solution of chromium nitrate, 1 to 1.2 times equivalent of 10% aqueous ammonia is dropwise added. Properties of chromium hydroxide can be controlled by adjusting a reaction rate of the precipitation reaction. The higher reaction rate, the better. The reaction rate depends on a temperature of the reaction system, a method of mixing the aqueous ammonia (i.e. a mixing speed), stirring conditions, etc.

Precipitated chromium hydroxide is dried, for example, in an air, at a temperature of 70 to 200° C., in particular around 120° C., for 1 to 100 hours, in particular around 12 hours. The catalyst at this stage is referred to as a "chromium hydroxide state catalyst". This catalyst is powdered to 1 mm or smaller. An amount of powder having a particle size of 46 to 1000 $\mu$m is preferably about 95%.

The precipitation reaction rate is adjusted so that a powder density is from 0.6 to 1.1 g/ml, preferably from 0.6 to 1.0 g/ml. When the powder density is smaller than 0.6 g/ml, strength of a pellet produced from the powder is not sufficient. When the powder density is larger than 1.1 g/ml, the catalyst has low activity.

The specific surface area of the powder is at least 100 m$^2$/g, preferably at least 120 m$^2$/g after degassed at 200° C. for 80 minutes. The upper limit of the specific surface area of the powder is preferably 220 m$^2$/g.

The chromium hydroxide powder which contains optionally 3% by weight or less of graphite is pelletized by a pelletizer. Preferably, a pellet has a diameter of 3.0 mm and a height of 3.0 mm, and a crushing pressure (i.e. strength of the pellet) of 210±40 Kg/cm$^2$. When the crushing pressure is too large, a contact efficiency of the gas and also the catalytic activity decrease, and the pellet tends to be easily cracked. When the crushing pressure is too small, the pellet is easily powdered so that handleability of the pellet is deteriorated.

The formed catalyst is then sintered in an atmosphere of an inert gas, for example, in a stream of nitrogen to obtain amorphous chromium oxide. A sintering temperature is usually at least 360° C. But, since too high sintering temperature will crystallize chromium oxide, the sintering temperature should be as high as possible in a temperature range in which chromium oxide is not crystallized. Preferably, the sintering is carried out at a temperature of 380 to 460° C., in particular around 400° C. for 1 to 5 hours, in particular around 2 hours.

The sintered catalyst has a specific surface area of from 170 m$^2$/g to 300 m$^2$/g, preferably from 180 m$^2$/g to 280 m$^2$/g, more preferably from 200 m$^2$/g to 260 m$^2$/g. When the specific surface area is smaller than 170 m$^2$/g, the catalyst has an insufficient activity. As the surface area of the catalyst increases, the catalytic activity increases. But, above 300 m$^2$/g, the catalytic activity saturates. Preferably, the specific surface area does not exceed 280 m$^2$/g.

In the present invention, the specific surface area of chromium oxide catalyst is measured using "MONOSORB" (manufactured by Quanta Chrome).

The catalyst is preferably fluorinated, namely treated with hydrogen fluoride. The fluorination is carried out at a temperature at which water is not condensed, for example around 150° C. under a pressure of one atm. but not higher than the temperature at which the catalyst is not crystallized by a reaction heat. Preferably, the fluorination temperature is from 100 to 460° C. A pressure is not limited. The same pressure as in the catalytic reaction is preferably.

When the catalyst is not fluorinated, hydrogen fluoride will react with the catalyst and the desired reaction is greatly inhibited.

The fluorination of the catalyst is effected till a content of fluorine in the catalyst reaches at least 8% by weight. In order to prevent the inhibition of the desired reaction, the fluorine content is preferably at least 15% by weight. The upper limit of the fluorine content is usually 48% by weight. A specific surface area of the catalyst may be decreased by the fluorination.

By the process of the present invention, various halogenated hydrocarbons can be fluorinated. Specific examples of the halogenated hydrocarbon are trichloroethylene, 1,1,1-trifluorochloroethane (133a), carbon tetrachloride, chloroform, dichloromethane, chloromethane, 1,1,1-trichloroethane, trichlorotrifluoroethane (113a, 113), CF$_3$CHCl$_2$ (123), CF$_3$CHClF (124), perchloroethylene (CCl$_2$=CCl$_2$), and the like.

The products obtained by the process of the present invention are as follows:
1,1,1,2-tetrafluoroethane (134a) from 1,1,1-trifluorochloroethane,
114 from CCl$_2$=CCl$_2$ or 113,
115 from CCl$_2$=CCl$_2$, 113, 113a or 114a,
124 from CCl$_2$=CCl$_2$ or 123,
125 from CCl$_2$=CCl$_2$, 123 or 124,
32 from dichloromethane or chlorofluoromethane,
41 from chloromethane,
11 from carbon tetrachloride,
12 from carbon tetrachloride or trichloromethane,
141b from 1,1,1-trichloroethane,
142b from 1,1,1-trichloroethane or 141b,
143a from 1,1,1-trichloroethane, 141b or 142b.

One example of the reactions which occur in the process of the present invention is:

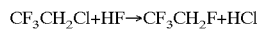

$$CF_3CH_2Cl + HF \rightarrow CF_3CH_2F + HCl$$

A molar ratio of hydrogen fluoride to the halogenated hydrocarbon and the reaction temperature are selected according to the characteristics of each reaction. In general, the molar ratio of hydrogen fluoride to the halogenated hydrocarbon is from 0.9:1 to 16:1. The reaction temperature is usually from 80 to 450° C. A preferred reaction pressure depends on a kind of reaction.

For example, in the reaction for preparing 134a from 133a, a conversion and a catalyst life can be adjusted by changing the molar ratio of hydrogen fluoride to 133a and the reaction temperature. A preferred molar ratio of hydrogen fluoride to 133a is from 0.9:1 to 10:1, and a preferred reaction temperature is from 290 to 380° C. The reaction pressure is preferably atmospheric pressure. Under the elevated pressure, the catalyst activity may be decreased.

PREFERRED EMBODIMENTS OF THE INVENTION

The present invention will be explained further in detail by following examples.

In following Examples 1–8 and Comparative Examples 1–5, 133a was fluorinated with hydrogen fluoride to prepare 134a.

As a reactor tube, a Hasteloy C tube having an inner diameter of 15 mm was used.

In Examples 1–3 and Comparative Examples 1–3, the catalyst was pelletized and ground to a powder having a particle size of 300 to 1000 $\mu$m.

In Examples and Comparative Examples, catalytic activity, a selectivity, a catalyst life and a throughput were compared. Unless otherwise defined, the catalytic activity, the catalyst life and the throughput are defined as follows:

The catalytic activity is the achieved maximum conversion (%).

The catalyst life is a time (hr) at which the conversion decreased to 60% of the maximum value.

The throughput is an amount of the reaction product (134a) produced per one liter of the catalyst per one hour.

EXAMPLE 1

To a 5.7% aqueous solution of chromium nitrate (765 Kg), 10% aqueous ammonia (114 Kg) was added over 2 minutes 10 seconds. The precipitate was collected by filtration and dried in an air at 120° C. for 12 hours to obtain chromium hydroxide. Chromium oxide was molded to obtain pellets each having a diameter of 3.0 mm and a height of 3.0 mm and sintered at 400° C. for 2 hours to obtain amorphous chromium oxide. Then, amorphous chromium oxide was fluorinated with hydrogen fluoride at 200° C. for 2 hours to obtain a catalyst having a fluorine content of 15.6% by weight.

Figure 1B:
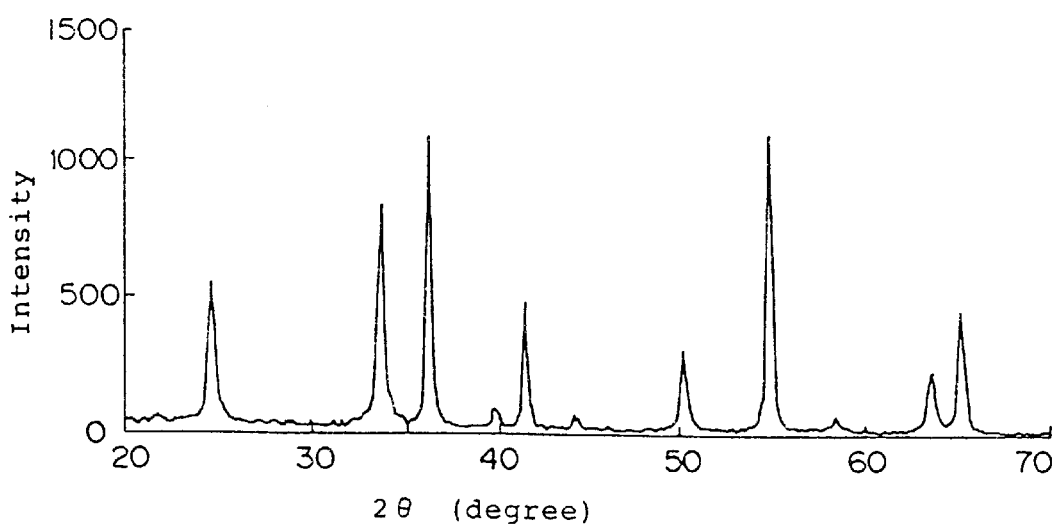

Chromium hydroxide and amorphous chromium oxide had the following properties:

Chromium hydroxide
  Powder density: 0.80 g/ml
  Pellet strength: 241 kg/cm$^2$
  Specific surface area: 180 m$^2$/g
Chromium oxide
  Specific surface area: 241 m$^2$/g FIG. 1A shows an X-ray diffraction pattern of chromium oxide prepared above. FIG. 1B shows an X-ray diffraction pattern of crystalline chromium oxide. From the comparison of these two diffraction patterns, it is understood that chromium oxide prepared in this Example was amorphous since FIG. 1A has no peak.

Using the amorphous chromium oxide catalyst, the fluorination of 133a was carried out under the following conditions:

Molar ratio (HF:133a): 9:1
Reaction temperature: 350° C.
Contact time: 0.5 (gsec/Nml)
(A ratio of a catalyst weight W to a flow rate F).
The catalytic activity was 26.9%.

Comparative Example 1

In the same manner as in Example 1 but changing the precipitation conditions (a 5.7 wt. % aqueous solution of chromium nitrate (255 Kg), 10% aqueous ammonia (38 Kg) and the addition time of 9 minutes 45 seconds), a catalyst was prepared. Chromium hydroxide and chromium oxide had the following properties:

Chromium hydroxide
  Powder density: 1.19 g/ml
  Pellet strength: 93 kg/cm$^2$
  Specific surface area: 79 m$^2$/g
Chromium oxide
  Specific surface area: 126 m$^2$/g 133a was fluorinated in the same manner as in Example 1 but using above chromium oxide. The catalytic activity was 7.4%.

EXAMPLE 2

A catalyst was prepared as follows:

To a 5.7 wt. % aqueous solution of chromium nitrate (25.5 Kg), 10% aqueous ammonia (3.8 Kg) was added at 50° C. Then, a catalyst was prepared in the same manner as in Example 1.

Chromium hydroxide and chromium oxide had the following properties:

Chromium hydroxide
  Powder density: 0.67 g/ml
  Pellet strength: 178 kg/cm$^2$
  Specific surface area: 141 m$^2$/g
Chromium oxide
  Specific surface area: 221 m$^2$/g When 133a was fluorinated at a molar ratio of 9:1, a reaction temperature of 350° C. and a contact time of 0.5, the catalytic activity was 17.3%.

When 133a was fluorinated at a molar ratio of 1:1, a reaction temperature of 350° C. and a contact time of 0.4, the catalyst life was 115 hours.

Comparative Example 2

In the same manner as in Example 2 but changing a precipitation temperature to 33° C., a catalyst was prepared. Chromium hydroxide and chromium oxide had the following properties:

Chromium hydroxide
  Powder density: 0.53 g/ml
  Pellet strength: 303 kg/cm$^2$
  Specific surface area: 134 m$^2$/g
Chromium oxide
  Specific surface area: 154 m$^2$/g 133a was fluorinated in the same manner as in Example 2 but using above chromium oxide. The catalytic activity was 16.5% and the catalyst life was 89 hours.

EXAMPLE 3

To a 5.9 wt. % aqueous solution of chromium chloride (16.3 Kg), 10% aqueous ammonia (3.2 Kg) was added at 50° C. Then, a catalyst was prepared in the same manner as in Example 1. Chromium hydroxide and chromium oxide had the following properties:

Chromium hydroxide
  Powder density: 0.62 g/ml
  Pellet strength: 246 kg/cm$^2$
  Specific surface area: 158 m$^2$/g
Chromium oxide
  Specific surface area: 228 m$^2$/g When 133a was fluorinated at a molar ratio of 9:1, a reaction temperature of 350° C. and a contact time of 0.5, the catalytic activity was 19.2%.

When 133a was fluorinated at a molar ratio of 1:1, a reaction temperature of 350° C. and a contact time of 0.4, the catalyst life was 106 hours.

Comparative Example 3

In the same manner as in Example 3 but changing a precipitation temperature to 33° C., a catalyst was prepared. Chromium hydroxide and chromium oxide had the following properties:

Chromium hydroxide
  Powder density: 0.41 g/ml
  Pellet strength: 220 kg/cm$^2$
  Specific surface area: 48 m$^2$/g
Chromium oxide
  Specific surface area: 122 m$^2$/g 133a was fluorinated in the same manner as in Example 3 but using above chromium oxide. The catalytic activity was 6.7% and the catalyst life was 80 hours.

EXAMPLE 4

Using the same catalyst as prepared in Example 2 except that the catalyst was used in the pellet form, 133a was fluorinated at a molar ratio of 4:1, a reaction temperature of 350° C. under one atm. at a conversion of 20%. A selectivity was 91.2%, a space velocity (SV) was 4557/hr, and a throughput was 1078 g/liter-catalyst/hr.

Comparative Example 4

In the same manner as in Example 4 but using a non-supported type chromium oxide (disclosed in Example 1 of GB 1 589 924 or corresponding Japanese Patent Kokai Publication No. 105404/1978), 133a was fluorinated. A selectivity was 91%, SV was 500/hr and the throughput was 82.9 g/liter-catalyst/hr.

EXAMPLE 5

Using the same catalyst as prepared in Example 2 except that the catalyst was used in the pellet form, 133a was fluorinated at a molar ratio of 4.6:1, a reaction temperature of 330° C. under one atm. at a conversion of 20.3%. selectivity was 95.7%, SV was 2250/hr, and a throughput was 483 g/liter-catalyst/hr.

Comparative Example 5

133a was fluorinated in the same manner as in Example 5 but using a supported type chromium oxide which is disclosed in Example 1 of WO89/10341 and prepared as follows:

In a solution of $CrCl_3 \cdot 6H_2O$ (191.5 g) in water (132 ml), activated alumina (400 g) was dipped. Then, alumina was dried at 90° C. on a water bath, at 110° C. in an air for 3 hours and at 400° C. for 3 hours. A calculated composition of the catalyst was 12% by weight of $Cr_2O_3$ and 88% by weight of $Al_2O_3$. The catalyst was fluorinated under the following conditions:

Hydrogen fluoride: 25 to 100% by mole

Temperature: 250 to 420° C.

SV: 400/hr

Time: 15 hours.

A selectivity was 94.3%, SV was 101/hr and the throughput was 15.6 g/liter-catalyst/hr.

EXAMPLE 6

Figure 2:
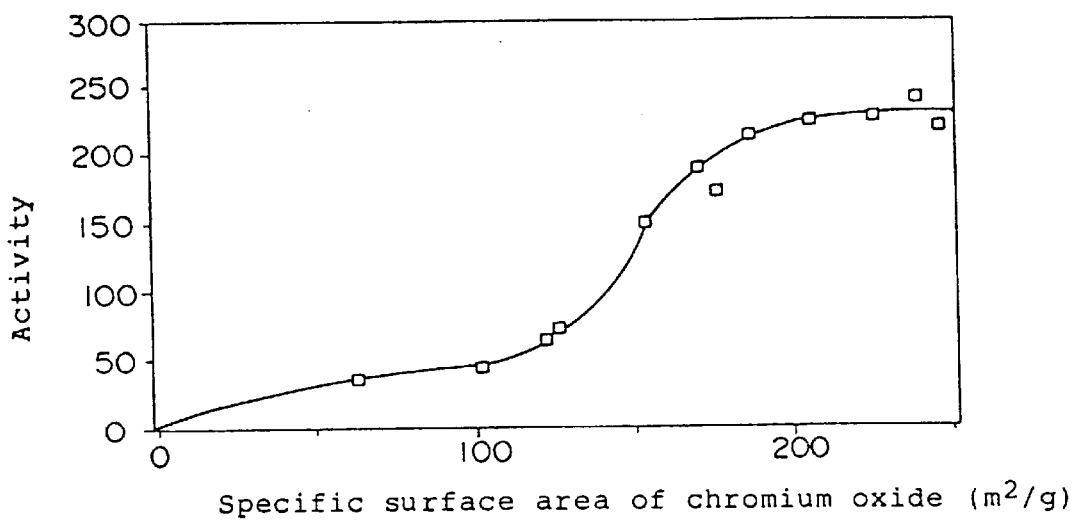
FIGS. 2, 3 and 4 compare the catalytic activities of the various chromium catalysts disclosed.

Using pellet-form chromium oxide catalysts having different specific surface areas, 133 a was fluorinated with hydrogen fluoride at a molar ratio of 9:1, a reaction temperature of 350° C. and a contact time of 0.5, and a catalytic activity was measured. The results are shown in FIG. 2.

In this Example and subsequent Examples, the catalytic activity is defined as a reaction speed at 350° C. The catalytic activity is expressed as a relative value.

EXAMPLE 7

Figure 3:
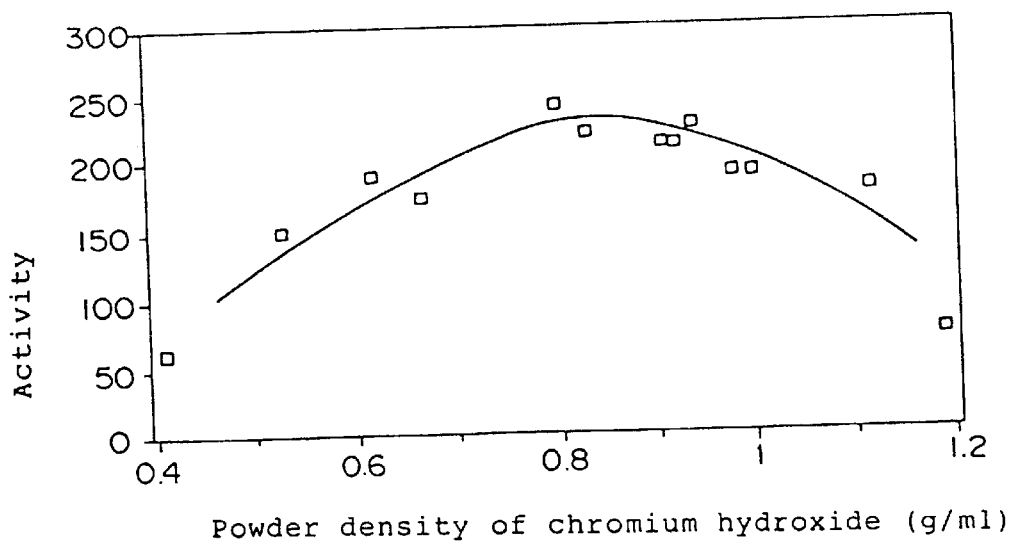

Using pellet-form chromium oxide catalysts which were prepared from chromium hydroxide having different powder densities, 133a was fluorinated with hydrogen fluoride at a molar ratio of 9:1, a reaction temperature of 350° C. and a contact time of 0.5, and a catalytic activity was measured. The results are shown in FIG. 3.

EXAMPLE 8

Figure 4:
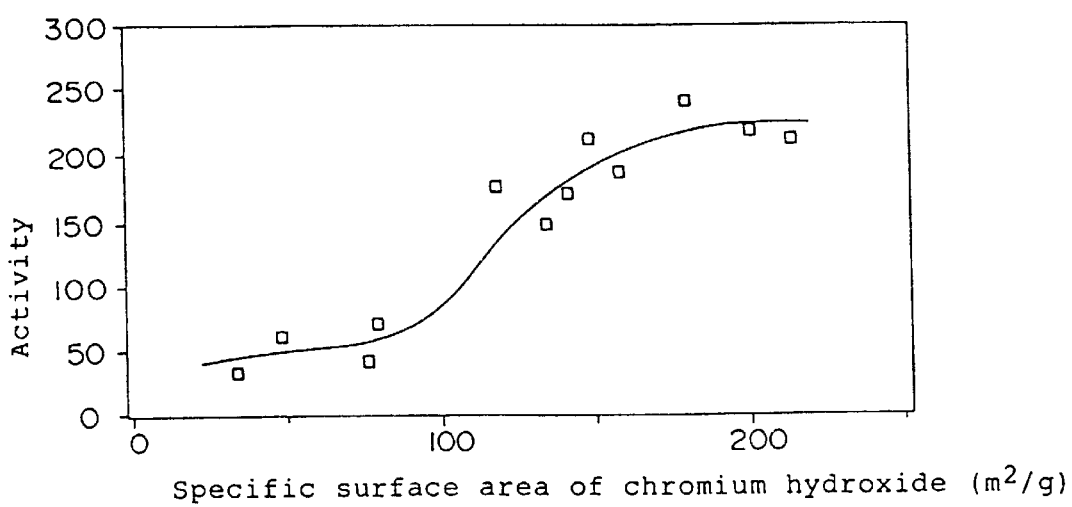

Using pellet-form chromium oxide catalysts which were prepared from chromium hydroxide having different specific surface areas, 133a was fluorinated with hydrogen fluoride at a molar ratio of 9:1, a reaction temperature of 350° C. and a contact time of 0.5, and a catalytic activity was measured. The results are shown in FIG. 4.

In Example 9, perchloroethylene was fluorinated and in Example 10, dichloromethane was fluorinated.

EXAMPLE 9

In a Hasteloy C made reactor tube having an inner diameter of 15 mm, the catalyst which was prepared in the same manner as in Example 2 and had a particle size of 300 to 600 $\mu$m (7 g) was charged. Through the reactor tube, hydrogen fluorinde and perchloroethylene were flowed at flow rates of 190 Nml/min. and 19 Nml/min., respectively and reacted at 350° C.

A conversion of perchloroethylene was 92%, and selectivities of 1,1-dichloro-2,2,2-trifluoroethane, 1-chloro-1,2,2, 2-tetrafluoroethane and pentafluoroethane were 20%, 28% and 44%, respectively.

EXAMPLE 10

In a Hasteloy C made reactor tube having an inner diameter of 15 mm, the catalyst which was prepared in the same manner as in Example 2 and in the pellet form (4 g) was charged. Through the reactor tube, hydrogen fluorinde and dichloromethane were flowed at flow rates of 360 Nml/min. and 90 Nml/min., respectively and reacted at 275° C.

A conversion of dichloromethane was 62%, and selectivities of fluorochloromethane and difluoromethane were 20% and 80%, respectively.

What is claimed is:

1. A process for fluorinating a halogenated hydrocarbon comprising reacting the halogenated hydrocarbon with hydrogen fluoride in the presence of a fluorination catalyst comprising chromium oxide having a specific surface area of from 170 $m^2/g$ to 300 $m^2/g$.

2. The process according to claim 1, wherein chromium oxide is amorphous.

3. The process according to claim 1, wherein chromium oxide is pre-treated by fluorination.

4. The process according to claim 3, wherein pre-treated chromium oxide contains at least 8% by weight of fluorine.

5. The process according to claim 1, wherein said halogenated hydrocarbon is trichloroethylene.

6. The process according to claim 1, wherein said halogenated hydrocarbon is 1,1,1-trifluorochloroethane.

7. The process according to claim 6, wherein a reaction temperature is from 290 to 380° C.

8. The process according to claim 1, wherein said halogenated hydrocarbon is perchloroethylene.

9. The process according to claim 1, wherein said halogenated hydrocarbon is dichloromethane.

10. The process according to claim 1, wherein before the halogenated hydrocarbon is reacted with hydrogen fluoride in the presence of a fluorination catalyst, the fluorination catalyst is prepared by the steps of:

mixing an aqueous solution of a chromium salt with aqueous ammonia to precipitate chromium hydroxide, drying and pelletizing precipitated chromium hydroxide, and sintering pelletized chromium hydroxide to obtain the chromium oxide catalyst.

11. The process according to claim 10, wherein the pelletized chromium hydroxide is sintered at a temperature of 380° C. to 460° C.

12. The process according to claim 10, wherein said chromium oxide fluorination catalyst is prepared by drying and pelletizing said chromium hydroxide at a temperature of 70° C. to 200° C.

13. The process according to claim 1, wherein the specific surface area of the catalyst is from 180 m$^2$/g to 280 m$^2$/g.

14. The process according to claim 1, wherein the specific surface area of the catalyst is from 200 m$^2$/g to 260 m$^2$/g.

15. The process according to claim 10, wherein the chromium hydroxide is precipitated at a rate such that a powder density thereof is from 0.6 to 1.1 g/ml.

16. The process according to claim 10, wherein the chromium hydroxide is precipitated at a rate such that a powder density thereof is from 0.6 to 1.0 g/ml.

17. The process according to claim 1, wherein the halogenated hydrocarbon is completely fluorinated so that all of the halogen atoms are converted to fluorine atoms.

18. The process according to claim 17, wherein said halogenated hydrocarbon is selected from the group consisting of trichloroethylene, 1,1,1-trifluorochloroethane, perchloroethylene, and dichloromethane.

19. The process according to claim 18, wherein the specific surface area of the catalyst is from 180 m$^2$/g to 280 m$^2$/g.

20. The process according to claim 18, wherein the specific surface area of the catalyst is from 200 m$^2$/g to 260 m$^2$/g.

* * * * *